United States Patent [19]

Overgaard et al.

[11] Patent Number: 5,424,482
[45] Date of Patent: Jun. 13, 1995

[54] PROCESS FOR PREPARING COLOR-STABLE TERTIARY BUTYLDIETHANOLAMINE

[75] Inventors: Thomas H. Overgaard, Redford Township; Louis P. Verduce, Wyandotte, both of Mich.

[73] Assignee: Elf Atochem N.A., Inc., Philadelphia, Pa.

[21] Appl. No.: 742,780

[22] Filed: Aug. 8, 1991

[51] Int. Cl.⁶ .................. C07C 209/90; C07C 209/84
[52] U.S. Cl. ........................................ 564/2; 564/497; 564/498; 564/499
[58] Field of Search .................. 564/497, 498, 499, 2; 203/31, 32, 6

[56] References Cited

U.S. PATENT DOCUMENTS

| | | | |
|---|---|---|---|
| 3,207,790 | 9/1965 | Glew et al. | 260/584 |
| 3,453,183 | 7/1969 | Okubo et al. | 564/497 |
| 4,379,024 | 4/1983 | Gardner | 203/6 |

FOREIGN PATENT DOCUMENTS

| | | | |
|---|---|---|---|
| 2061939 | 5/1981 | United Kingdom | 564/497 |
| 228693 | 9/1961 | U.S.S.R. | 564/497 |

Primary Examiner—Shailendra Kumar

[57] ABSTRACT

Tertiary-butyldiethanolamine subject to color deterioration is purified and stabilized against color formation by vacuum distilling said amine at a pressure within the range of 1 to 50 mm.Hg (1–50 torr) in the absence of a reducing agent,

12 Claims, No Drawings

PROCESS FOR PREPARING COLOR-STABLE TERTIARY BUTYLDIETHANOLAMINE

BACKGROUND OF THE INVENTION

This invention concerns the treatment of tertiary butyldiethanolamine subject to color deterioration to remove color-forming contaminants and to stabilize the amine against color formation. More particularly, it concerns a process for treating said tertiary (t-)butyldiethanolamine by vacuum distillation.

To produce t-butyldiethanolamine, two moles of ethylene oxide are usually reacted with one mole of t-butylamine. If one desires to produce t-butylaminoethanol, one mole of ethylene oxide is reacted with one mole of t-butylamine. In this latter reaction, t-butyldiethanolamine is coproduced with t-butyl- aminoethanol. The crude products of these reactions are contaminated with impurities which include water and color-forming bodies. In the production of t-butylaminoethanol, the coproduced t-butyldiethanolamine, in the past, has been discarded because there was no satisfactory method for purifying it.

There is a need for high purity/low color t-butyldiethanolamine in the chemical market. The product is used in photographic and other chemical processes as a reaction component. Previously, obtaining this product which is both chemically pure and substantially color-free in a commercially successful process has not been realized.

PRIOR ART

U.S. Pat. No. 3,207,790 discloses the reduction of color in discolored alkanolamines by mixing into the off-color amine a quantity of an alkali metal borohydride and subsequently distilling under reduced pressure.

U.S. Pat. No. 4,379,024 discloses the preparation of color-free alkylaminoalkanols by the addition of an alkali metal borohydride to the crude material (unpurified). A final step of purification of the aminoalkanol includes distillation at a reduced pressure (in excess of 100 mm.Hg).

In U.S. Ser. No. 07/587,198 filed Sep. 24, 1990 a process for the purification of off-color N—($C_4$-$C_{10}$-)di($C_2$-$C_3$) alkanolamines is disclosed wherein a water-soluble metal borohydride is added and the off-color product subjected to vacuum distillation at a pressure of less than 50 mm.Hg in the presence of water.

In U.S. Pat. No. 3,453,183, a method of purifying ethanolamines is disclosed wherein powdered silicas, powdered silicates, liquid silicates or powdered aluminas is added to the ethanolamine and the material is subjected to vacuum distillation. While low pressure distillation is not taught in this patent to be critical for color stabilization (100-1 mm.Hg range), pressures of 5-50 mm.Hg are disclosed for the purpose of fractionating the mono-, di- and triethylamine mixture.

The prior art processes have not been found, for reasons unknown, to be useful for obtaining a high purity, low color t-butyldiethanolamine.

STATEMENT OF THE INVENTION

This invention is a process for the preparation of a high purity, low color product from contaminated tertiary-butyldiethanolamine, subject to color deterioration, by vacuum distillation at a pressure within the range of 1 to 50 mm.Hg in the absence of a reducing agent.

DETAILED DESCRIPTION OF THE INVENTION

Using the techniques known in the prior art, various aminoalkanols and alkanolamines containing impurities which produce color are readily purified and decolored. Attempting to purify and decolor (or color stabilize) the specific compound t-butyldiethanolamine with prior art methods has not been successful for reasons unknown.

It has now been found that t-butyldiethanolamine can be highly purified and color stabilized (made permanently, substantially color-free at temperatures below 70° C.) by vacuum distilling said amine at a pressure ranging from 1 to 50 mm.Hg, preferably about 10 mm.Hg in the absence of a reducing agent.

In the preferred form of this invention, the t-butyldiethanolamine is distilled in a verticle column containing means to promote vapor to vapor or vapor to liquid contact, e.g., plates equipped with bubble caps (5-25 plates, preferably 6-15 plates, most preferably about 6), packings of ceramic or stainless steel rings, saddles, grids or screens, ballast trays or the like, and combinations of these contact promoting means. Distillation is carried out at a ratio [volume of liquid (vapor) taken off as overhead vs. volume of liquid returned to distillation column] of 1:3 to 3:1, more preferably from 1:2 to 2:1, and most preferably 1:1. The bottom temperature of the distillation column is maintained at less than 200° C., ie., from about 160° to 195° C. and preferably 165° to 175° C. The overhead temperature of the column generally ranges from 140° to 190° C. and preferably from 140° to 170° C. The take-off temperature of the t-butyldiethanolamine product from the distillation column is between about 42° and about 75° C., more preferably from 50° to 60° C. and most preferably about 55° C.

The use of low pressure reduces the maximum temperature to which the t-butyldiethanolamine must be subjected for purification during distillation thus providing a purification process which is operated at sufficiently low temperature to avoid reformation of color-forming bodies. In the preferred embodiment of the invention, by utilization of the proper conditions and equipment, the crude t-butyldiethanolamine is distilled with a relatively short residence time in the heated zone. This, coupled with the use of low pressure and the absence of a reducing agent, produces a high yield of product of high purity and substantially no color.

The following examples are set forth to demonstrate the process of this invention.

EXAMPLE 1

Experiments were conducted representative of the prior art processes and demonstrating the failure of such processes to purify t-butyldiethanolamine. The distillation apparatus used in these processes is as follows: The apparatus consisted of a 2 liter flask, glascol heating mantle, thermometer well and a vacuum jacketed 25 plate Oldershaw column. For some experiments the Oldershaw column was reduced to 15 plates by removing the upper column section. Attached to the column was a distilling head adapter followed by a Friedrich's water condenser. The down leg of the adapter was connected in series to a straight bore stopcock, an Allihn condenser, a vacuum adapter and a 500 ml. receiver. A 5 port vacuum manifold was attached to a closed end manometer, dry ice trap, micro valve and both condensers. To prevent the product from solidifying prior to entering the receiver, the upper adapter, stopcock and vacuum adapter were insulated. Warm water circulated through the Allihn condenser.

Five one gallon cans of a contaminated t-butyldiethanolamine (off-color product) were used as the feedstock for all distillations. This product had an assay of 99.49%, a water content of 0.3% and an absorptivity of $\geq 0.088$ ml./gms maximum at 410 nanometers (nm.) and $\geq 0.046$ ml./gms maximum at 470 nm.

Experiments A and B 1000 ml. of off-color product was charged to the 2 liter flask of the apparatus which contained 10 ml. of a 12% solution of sodium borohydride (NaBH$_4$). The distillation, using a 25 plate column, was maintained at 50 mm Hg pressure with a bottom (2 liter flask) temperature of 198° C. and a 4:1, column/receiver, reflux ratio. After thoroughly cleaning the apparatus, Experiment A was repeated as Experiment B. In both experiments, fractional cuts were periodically taken and analyzed by gas chromatography (GC). The results are shown in Tables 1 and 2.

Experiments C and D

The same apparatus (thoroughly cleaned) and procedure were used in this experiment as in Experiments A & B except that 2 grams of ethylenediamine and 10 ml of water was used to replace the borohydride solution of Experiment A, and a reflux ratio of 1:1 was used. After thoroughly cleaning the apparatus, Experiment C was repeated as Experiment D. In both C and D, fractional cuts were periodically taken and analyzed by GC. The results are shown in Tables 1 and 2.

EXAMPLE 2

Experiments E, F and G were conducted to demonstrate the process of this invention. The apparatus of Example 1, thoroughly cleaned between experiments, was employed. In these experiments, the process conditions were as in Experiment A except that no additives were used; in Experiment E, the reflux ratio was 2:1; in Experiment F, the reflux ratio was 1:1 and the number of plates were reduced to 15 by removal of the upper column section; and, in Experiment G, the number of plates were 15 and the reflux ratio was 1:1. In all experiments, fractional cuts were periodically taken and analyzed by GC. The results are shown in Tables 1 and 2.

EXAMPLE 3

Experiments H and I were carried out to demonstrate the process of this invention operated under more preferred condition using the same apparatus as in Example 1 with thorough cleaning between experiments. The distillation pressure was 10 mm.Hg with a bottom temperature of 169° C.; the number of plates in the distillation column was 15; and the reflux ratio was 1:1. Distillation was carried out with 1000 ml of off-color product in the absence of an additive, i.e., no reducing agent or other additive present.

In both Experiments H and I, fractional cuts were periodically taken and analyzed by GC. The results are shown in Tables 1 and 2 below.

TABLE 1

| Experiment | Cut No. | Assay | % H$_2$O | Receiver, ML | Residue, ML | Comments |
|---|---|---|---|---|---|---|
| A | 1 | 67.78 | 23.19 | 48 | | Failed |
|   | 2 | 98.81 | 0.24 | 220 | | H$_2$O |
|   | 3 | 97.30 | 0.71 | 72 | | |
|   | 4 | 99.32 | 0.27 | 390 | | |
| B | 1 | 72.50 | 19.19 | 58 | | Failed |
|   | 2 | 98.43 | 0.33 | 275 | | H$_2$O & Assay |
|   | 3 | 86.32 | 11.05 | 44 | | |
|   | 4 | 69.39 | 22.92 | 40 | | |
|   | 5 | 98.34 | 0.42 | 105 | | |
|   | 6 | 94.10 | 1.51 | 57 | | |
|   | 7 | 97.17 | 0.40 | 105 | | |
| C | 1 | 58.99 | 34.44 | 85 | | Color |
|   | 2 | 99.11 | 0.19 | 255 | | Medium to |
|   | 3 | 99.64 (avg.) | — | 225 | | Dark Brown |
|   | 4 | 99.81 | — | 360 | | |
| D | 1 | 85.86 | 4.88 | 78 | | Color |
|   | 2 | 99.03 | 0.06 | 310 | | Yellow to |
|   | 3 | 99.52 | 0.05 | 380 | | Medium Brown |
| E | 1 | 88.61 | 3.23 | 59 | | Passed - |
|   | 2 | 99.70 | 0.07 | 473 | | 75.0% yield |
|   | 3 | 99.21 | 0.16 | 277 | 160 | |
| F | 1 | 91.04 | 1.84 | 53 | | Color Passed |
|   | 2 | 99.36 | 0.06 | 160 | | (Visually) |
|   | 3 | 99.54 | 0.06 | 305 | | 81.8% yield |
|   | 4 | 99.84 | 0.05 | 295 | | |
|   | 5 | 99.89 | 0.07 | 58 | 75 | |
| G | 1 | 95.29 | 0.72 | 108 | | Passed - |
|   | 2 | 99.69 | 0.05 | 730 | 117 | 73% yield |
| H | 1 | 93.45 | 0.43 | 61 | | Passed - |
|   | 2 | 99.16 | 0.22 | 140 | | 83.5% yield |
|   | 3 | 99.67 | 0.12 | 320 | | |
|   | 4 | 99.92 | 0.03 | 375 | 59 | |
| I | 1 | 95.38 | 0.34 | 98 | | Passed - |
|   | 2 | 99.71 | 0.01 | 851 | 27 | 85.1% yield |

The ultra violet-visible (U.V./Vis.) absorptivity of a number of those distillation cuts taken in the experiments, which cuts were determined to have acceptable (or near acceptable) assay and reduced water content, was determined in accordance with the following equation:

$$\text{Absorptivity} = \frac{\text{Absorbance}}{\text{Cell Thickness} \times \frac{\text{Sample Weight}}{\text{Dilution Volume, ml.}}}$$

where cell thickness is 30 mm. and dilution volume is 5 g diluted to 25 ml. The results of the U.V./Vis. absorptivity determinations are found in the following Table 2.

TABLE 2

| Experiment and Cut Identification | Sample, gm. | Absorbance 470 nm | Absorbance 410 nm | Absorptivity 470 nm | Absorptivity 410 nm |
|---|---|---|---|---|---|
| B 2 | 5.0183 | .022 | .053 | .0037 | .0088 |
| B 5 | 5.0044 | .013 | .037 | .0022 | .0062 |
| C 4 | 5.0060 | .048 | .146 | .0080 | .0243 |
| E 2 | 5.0147 | .013 | .031 | .0022 | .0052 |
| G 2 | 5.0194 | .015 | .019 | .0025 | .0032 |
| H 4 | 5.0049 | .000 | .007 | .0000 | .0012 |
| I 2 | 5.0936 | .005 | .014 | .0008 | .0023 |

The distillation cut determined to have the lowest U.V./Vis. absorptivity in Table 2 (H4) was separated into four samples and each maintained at a different temperature for two weeks. At two weeks, the U.V./Vis. absorptivity of the samples was determined and the results are reported in the following Table 3.

TABLE 3

| Temp. °C. | ABSORPTIVITY 470 nm | ABSORPTIVITY 410 nm | Comments |
|---|---|---|---|
| 40 | .0005 | .0016 | Passed |
| 50 | .0007 | .0020 | Passed |
| 60 | .0013 | .0026 | Passed |
| 70 | .0056 | .0230 | Failed |

From the results of the above table, it appears that prolonged heating at 70° C. or higher will discolor the color stabilized t-butyldiethanolamine. Therefore, the stabilized product should not be subjected during storage for any time period to temperatures over 80° C. and prolonged temperatures of about 70° C. or over should be avoided.

EXAMPLE 4

This example demonstrates the process of this invention carried out in commercial equipment. Crude t-butyl diethanolamine originating from the manufacturing process and having most of the starting material, water catalyst and coproduced t-butylaminoethanol removed was fed to the middle of a steel, distillation column having a height of 18 feet and a diameter of 24 inches. The bottom 9 feet of the column was packed with 304 stainless steel rings while the top 9 feet was equipped with 304 stainless steel ballast trays. The crude product had an assay of about 98.5%, a water content of 0.1% and an off-color appearance. The crude was distilled at a pressure of 10 mm.Hg, a maximum bottom temperature of 169° C., a maximum overhead temperature of 145° C. and a reflux ratio of 1:1. The product take off temperature was 55° C. maximum. Analysis of the product determined that it had an assay of 99%+, and H2O (water) content of less than 0.2% and a U.V./Vis. absorptivity of less than 0.022 ml./g at 410 nm and less than 0.006 ml/g at 470 nm. The product yield was 85%.

Rectification of crude product from the same source in the same apparatus and under the same conditions except that the pressure was 50 mm. Hg, the maximum bottom temperature was 193° C., and the maximum overhead temperature was 184° C., provided an 83% yield of purified product of substantially the same specifications as the above 85% yield product.

We claim:

1. A process for preparing a high purity, low color product from contaminated tertiary butyldiethanolamine subject to color deterioration consisting essentially of heating said tertiary butyldiethanolamine under vacuum distillation at a pressure within the range of 1–50 mm. Hg. (1–50 torr) in the absence of an additive.

2. The process of claim 1 wherein said pressure is about 10 mm.Hg.

3. The process of claim 1 wherein vacuum distillation is effected in a verticle column having means to promote vapor to vapor or vapor to liquid contact and which has a bottom temperature ranging from about 160° to about 195° C. and an overhead temperature of from about 140° to about 190° C.

4. The process of claim 3 wherein said pressure is about 10 mm.Hg.

5. The process of claim 3 wherein said verticle column includes means to carry out distillation at a varying reflux ratio and the reflux ratio ranges from about 1:3 to about 3:1.

6. The process of claim 3 wherein said means are from 5 to 25 plates.

7. The process of claim 3 wherein said means are stainless steel ballast trays.

8. The process of claim 3 wherein said means are a plurality of ceramic or stainless steel rings or saddles.

9. The process by claim 5 wherein said pressure is about 10 mm.Hg and said reflux ratio is from 1:2 to 2:1.

10. The process of claim 9 wherein the bottom temperature is from 165° to 175° C. and the overhead temperature is from 140° to 170° C., and said verticle column includes means to take-off purified product at elevated temperature.

11. The process of claim 10 wherein said reflux ratio is 1:1, said column contains about 6 plates and the take-off temperature of the purified product from said column is between about 42° and about 75° C.

12. The process of claim 11 wherein said take-off temperature is from 50° to 60° C.

* * * * *